(12) United States Patent
Kurakami et al.

(10) Patent No.: US 8,969,618 B2
(45) Date of Patent: Mar. 3, 2015

(54) PROCESS FOR PRODUCING UNSATURATED ALDEHYDE AND/OR UNSATURATED CARBOXYLIC ACID

(75) Inventors: Tatsuhiko Kurakami, Yamaguchi (JP); Susumu Matsumoto, Gunma (JP); Atsushi Sudo, Gunma (JP); Kazuo Shiraishi, Gunma (JP); Masashi Hashiba, Gunma (JP)

(73) Assignee: NipponKayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/982,808

(22) PCT Filed: Jan. 16, 2012

(86) PCT No.: PCT/JP2012/050730
§ 371 (c)(1),
(2), (4) Date: Jul. 31, 2013

(87) PCT Pub. No.: WO2012/105304
PCT Pub. Date: Aug. 9, 2012

(65) Prior Publication Data
US 2013/0310604 A1 Nov. 21, 2013

(30) Foreign Application Priority Data
Feb. 2, 2011 (JP) ................................. 2011-020782
Feb. 2, 2011 (JP) ................................. 2011-020783

(51) Int. Cl.
C07C 51/25 (2006.01)
C07C 45/35 (2006.01)
C07C 51/235 (2006.01)
C07C 45/38 (2006.01)

(52) U.S. Cl.
CPC ............... *C07C 51/235* (2013.01); *C07C 45/35* (2013.01); *C07C 51/252* (2013.01); *C07C 45/38* (2013.01)
USPC .......................................... 562/547; 568/479

(58) Field of Classification Search
CPC .............................. C07C 45/35; C07C 51/252
See application file for complete search history.

(56) References Cited

U.S. PATENT DOCUMENTS

2005/0049435 A1 3/2005 Ha et al.

FOREIGN PATENT DOCUMENTS

| CN | 1845785 A | 10/2006 |
|---|---|---|
| CN | 101842341 A | 9/2010 |
| CN | 101848883 A | 9/2010 |
| EP | 1125911 A2 | 8/2001 |
| JP | 8-3093 A | 1/1996 |
| JP | 2001-226302 A | 8/2001 |
| JP | 2001-328951 A | 11/2001 |
| JP | 2004-2209 A | 1/2004 |
| JP | 2005-320315 A | 11/2005 |
| JP | 3775872 B | 5/2006 |
| JP | 2007-533605 A | 11/2007 |
| JP | 2009-114119 A | 5/2009 |
| WO | 2009/057463 A1 | 5/2009 |
| WO | 2009/060704 A1 | 5/2009 |

OTHER PUBLICATIONS

White et al, Basic Energy Sciences Advisory Committee Subpanel Workshop Report, Opportunities for Catalysis in the 21st Century, 2002, pp. 1-47.*
International Search Report and Written Opinion mailed Apr. 3, 2012 in corresponding PCT application No. PCT/JP2012/050730.
International Preliminary Report on Patentability mailed Aug. 15, 2013 in corresponding PCT application No. PCT/JP2012/050730.
European communication dated Aug. 28, 2014 in corresponding European patent application No. 12742461.2.
Chinese communication, with English translation, issued May 29, 2014 in corresponding Chinese patent application No. 201280007615.6.

* cited by examiner

*Primary Examiner* — Paul A Zucker
(74) *Attorney, Agent, or Firm* — Nields, Lemack & Frame, LLC

(57) ABSTRACT

A catalyst and a catalyst packing schedule are designed so that a relation between the raw material conversion rate at which the yield of the objective product becomes maximum and the raw material conversion rate at which a high and low correlation between maximum temperature of the catalyst layer present closest to a reaction gas inlet side Zin and maximum temperature of the catalyst layer present closest to a reaction gas outlet side Zout is reversed satisfies a specific condition of $0.5 \leq Cmax - Ccrs \leq 5$, in which Cmax: a raw material conversion rate at which yield of the objective products becomes maximum; and Ccrs: a raw material conversion rate at which, when maximum temperature of the catalyst layer Zin is regarded as Tin, maximum temperature of the catalyst layer Zout is regarded as Tout, and the raw material conversion rate is changed, a high and low correlation between Tin and Tout is reversed.

5 Claims, No Drawings

PROCESS FOR PRODUCING UNSATURATED ALDEHYDE AND/OR UNSATURATED CARBOXYLIC ACID

TECHNICAL FIELD

The present invention relates to a process for producing acrolein and acrylic acid by subjecting propylene to vapor-phase catalytic oxidation with molecular oxygen or a gas containing molecular oxygen or a process for producing methacrolein and methacrylic acid by subjecting isobutylene or tertiary butanol to vapor-phase catalytic oxidation with molecular oxygen or a gas containing molecular oxygen.

BACKGROUND ART

A process for producing a corresponding unsaturated aldehyde and unsaturated carboxylic acid using propylene, isobutylene, or tertiary butanol as a raw material has been industrially widely implemented, but generation of a local high temperature area (hot spot) in the catalyst layer has become a big problem. Since the generation of the hot spot results in a decrease in the catalyst life or a decrease in the yield due to an excessive oxidation reaction, and in a worst case, the occurrence of a runaway reaction, some technologies for suppressing the hot spot have been proposed. For example, Patent Document 1 discloses a technology of lowering hot spot temperature by using a catalyst in which activity is controlled by changing the supported amount and by using a catalyst in which activity is controlled by changing the baking temperature of the catalyst. Patent Document 2 discloses a technology of using a catalyst in which activity is controlled by changing the ratio of apparent density of the catalyst. Patent Document 3 discloses a technology of using a catalyst in which activity is controlled by changing the content of an inactive component of a catalyst molded body and also changing the occupying volume of the catalyst molded body, the kind and/or amount of an alkali metal, and the baking temperature of the catalyst. Patent Document 4 discloses a technology of providing reaction zones in which the occupying volume of the catalyst molded body is changed and mixing an inactive material into at least one reaction zone. Patent Document 5 discloses a technology of using a catalyst in which activity is controlled by changing the baking temperature of the catalyst. Patent Document 6 discloses a technology of using a catalyst in which activity is controlled by changing the occupying volume and baking temperature of the catalyst, and/or the kind and amount of an alkali metal.

BACKGROUND ART DOCUMENT

Patent Document

Patent Document 1: Japanese Patent No. 3775872
Patent Document 2: JP-A-2004-2209
Patent Document 3: JP-A-2001-328951
Patent Document 4: JP-A-2005-320315
Patent Document 5: JP-A-8-3093
Patent Document 6: JP-A-2001-226302

SUMMARY OF INVENTION

Problem that Invention is to Solve

Even when the suppression of the hot spot was tried by the above methods, the suppression was not yet satisfactory. Furthermore, there is a problem that expected catalyst performance and life are not always obtained in industrial plants and thus improvement has been desired. Examples include the following.

1) The method of using a catalyst in which the activity is controlled by changing the occupying volume of the catalyst is useful as a method of suppressing the hot spot but tens of thousands of reaction tubes are present in an industrial plant and, in the case that the inner diameter of the reaction tube is 20 mm to 30 mm, there may arise an error of about +0.2 mm to −0.2 mm. In the case of a catalyst having a small occupying volume, influence thereof is negligible but, in the case of a catalyst having a large occupying volume, i.e., a catalyst having a large particle diameter, it is found that the influence cannot be negligible in some cases. Specifically, there may be mentioned a fact that the catalyst forms a bridge in the reaction tube at packing and a large effort is required for its correction, a fact that a difference in pressure loss among the reaction tubes is prone to be uneven depending on the packed amount and a change in the packing density and thus the difference causes localization of the raw material gas flow, and a fact that a large effort is also required for its correction. In the case where the catalyst shape is not spherical, it can be easily imagine that this problem becomes more remarkable.

2) Furthermore, in an industrial plant, there may arise not only the unevenness in the diameter of the reaction tube as mentioned above but also unevenness in heat-removing ability derived from the structure of the reactor, a distribution of heating medium temperature in horizontal and vertical directions, and a distribution of gas flow rate among the reaction tubes, and it is almost impossible that the catalyst is used in the same state in all the reaction tubes. Upon the analysis of the catalyst used in an industrial plant, the present inventors have found reaction tubes in which the catalyst at the raw material gas inlet area is intensively deteriorated, reaction tubes in which the catalyst is gently deteriorated over the whole area, and surprisingly, reaction tubes in which the catalyst at the raw material gas outlet area is more deteriorated than that at the inlet area. This fact suggests a possibility that the hot spot temperature of the catalyst layer at the raw material gas outlet side was abnormally high, and there is a risk of a runaway reaction in the worst case. This is attributable to a difference in the conversion rate of the raw material hydrocarbon and a difference in the shape of the temperature distribution resulting from the unevenness in the diameter of the reaction tube, the unevenness in heat-removing ability derived from the structure of the reactor, the distribution of the heating medium temperature in horizontal arid vertical directions, and the distribution of the gas flow rate among the reaction tubes in the aforementioned industrial plant. Thus, it is mentioned as a problem to develop a technology capable of maintaining high yields safely and steadily over a long period of time even in the industrial plant.

Means for Solving Problem

In an industrial plant, it is preferred to run it in a conversion rate at which a maximum yield is achieved and for many reaction tubes, a catalyst is selected so as not to exceed upper limit use temperature of the catalyst used at the conversion rate of the raw material. However, since there exists deviation of reaction conditions in the aforementioned industrial plant, the inventors have discovered the fact that there is a reaction tube in which the conversion rate of a raw material such as propylene becomes small in the whole reactor and the temperature of the catalyst layer at the raw material gas outlet side Zout sometimes exceeds the upper limit use temperature of the catalyst, and as a result, there are insufficient in the reaction yield, insufficient in the catalyst life, and a risk of a runway reaction. As a method for solving the problem, they have found that the above problem can be solved by designing a catalyst and a catalyst packing schedule so that a relation between the raw material conversion rate at which the yield of the objective product becomes maximum and the raw material conversion rate at which a high and low correlation between maximum temperature of the catalyst layer present closest to the reaction gas inlet side and maximum temperature of the catalyst layer present closest to the reaction gas outlet side is reversed satisfies a specific condition in the process of using a reaction tube on which a plurality of catalyst layers formed in a raw material gas flow direction, and thus have accomplished the invention.

Namely, the invention is as follows:

(1) A process for producing acrolein and acrylic acid or methacrolein and methacrylic acid by subjecting propylene or at least one kind selected from isobutylene and tertiary butanol to vapor-phase catalytic oxidation with a gas containing molecular oxygen using a fixed bed multitubular reactor, the process comprising:

A) providing a plurality of catalyst layers formed by division into N, where N represents an integer of 2 or more, in a raw material gas flow direction of reaction tubes and regarding the catalyst layer present closest to a reaction gas inlet side among the catalyst layers as Zin and the catalyst layer present closest to a reaction gas outlet side among the catalyst layers as Zout; and B) packing a catalyst so that activity of the catalyst packed in Zout becomes higher than activity of the catalyst packed in Zin to satisfy the following expression (1):

$$0.5 \leq Cmax - Ccrs \leq 5 \qquad \text{expression (1)}$$

Cmax: a raw material conversion rate at which yield of the objective products becomes maximum; and Ccrs: a raw material conversion rate at which, when maximum temperature of the catalyst layer Zin is regarded as Tin, maximum temperature of the catalyst layer Zout is regarded as Tout, and the raw material conversion rate is changed, a high and low correlation between Tin and Tout is reversed.

(2) The process for producing acrolein and acrylic acid or methacrolein and methacrylic acid according to (1), wherein N is 3 or less, baking temperature of the catalyst packed in Zin is higher than baking temperature of the catalyst packed in Zout, and a mixture of the catalyst and a molded body of an inactive material is packed in Zin.

(3) The process for producing acrolein and acrylic acid or methacrolein and methacrylic acid according to the above (1) or (2), wherein the catalyst is a spherical supported catalyst obtained by supporting an active powder on an inactive material.

(4) The process for producing acrolein and acrylic acid or methacrolein and methacrylic acid according to any one of the above (1) to (3), wherein particle diameter of the catalyst packed in each catalyst layer is the same over all the layers.

Effects of Invention

According to the invention, it becomes possible to produce acrolein and acrylic acid or methacrolein and methacrylic acid safely and steadily in high yields, in which a phenomenon of occurrence of an abnormal reaction induced by the fact that there exists a reaction tube in which the raw material conversion rate becomes low due to an event peculiar to an industrial plant and, as a result, the temperature of the catalyst packed in the reaction tube is considerably higher at the raw material gas outlet side than at the raw material gas inlet side, although a usual industrial plant is run at a raw material conversion rate at which a maximum yield is obtained unless exceptional circumstances exist, the catalyst packed in most reaction tubes reacts at a desired raw material conversion rate, and as a result, the hot spot temperature of the catalyst layer at the raw material gas inlet area is higher than the hot spot temperature of the catalyst at the raw material gas outlet side.

EMBODIMENTS FOR CARRYING OUT THE INVENTION

The following will describe preferable embodiment for carrying out the invention.

The catalyst of the invention itself can be prepared by a known method and is represented by the following general formula:

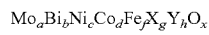

$$Mo_a Bi_b Ni_c Co_d Fe_f X_g Y_h O_x$$

wherein Mo, Bi, Ni, Co and Fe represent molybdenum, bismuth, nickel, cobalt and iron, respectively; X represents at least one element selected from tungsten, antimony, tin, zinc, chromium, manganese, magnesium, silica, aluminum, cerium and titanium; Y represents at least one element selected from potassium, rubidium, thallium and cesium; and a, b, c, d, f., g, h and x represent the numbers of atoms of molybdenum, bismuth, nickel, cobalt, iron, X, Y and oxygen, respectively, such that a=12, b=0.1 to 7, preferably b=0.5 to 4, c+d=0.5 to 20, more preferably c+d=1 to 12, f=0.5 to 8, further preferably f=0.5 to 5, g=0 to 2, particularly preferably g=0 to h=0.005 to 2, most preferably h=0.01 to 0.5, and x is a value determined by the oxidation state of the individual elements.

Here, a powder containing a catalyst active component is prepared by a known method such as a co-precipitation method or a spray drying method. The catalyst active component (hereinafter referred to as pre-baked powder) can be obtained by baking the obtained powder at preferably 200 to 600° C., more preferably 300 to 500° C. preferably in an air or nitrogen stream.

The pre-baked powder thus obtained can be used as a catalyst as it is, but is molded to form the catalyst of the invention in consideration of production efficiency and workability. The shape of the molded one is not particularly limited, such as a spherical shape, a cylindrical shape, or a ring shape. The shape should be selected in consideration of production efficiency, mechanical strength, and the like of the catalyst but a spherical shape is preferable. At the molding, it is common to use a single pre-baked powder and mold it but it may be possible to mix separately prepared granular pre-baked powders having different compositions of components such as iron, cobalt, nickel and alkali metals in an any ratio beforehand and mold the mixture or it may be possible to adopt a method where operations of supporting different kinds of pre-baked powders on an inert support are repeated to mold the pre-baked powders as plural layers. In this connection, at the molding, it is preferable to mix a molding aid such as crystalline cellulose and/or a strengthening agent such as ceramic whisker. The amount of the molding aid and/or the strengthening agent to be used is preferably 30% by weight or less, respectively. Moreover, the molding aid and/or the strengthening agent may be mixed with the above pre-baked powder in advance before the molding or may be added simultaneously, before, or after the addition of the pre-baked powder to a molding machine.

A molding method is not particularly limited but a method of using a tableting machine, an extrusion machine, or the like is preferable at the molding into a cylindrical shape or a ring shape.

More preferable is the case of molding into a spherical shape. It may be possible to mold the pre-baked powder into a spherical shape in a molding machine but a method of supporting the pre-baked powder (including the molding aid and the strengthening agent according to needs) on a support such as an inert ceramic is preferable. Here, the supporting method is not particularly limited as long as it is a method capable of supporting the pre-baked powder on the support uniformly, such as a tumbling granulation method, a method of using a centrifugal fluid coating apparatus, or wash coating. In consideration of production efficiency and the like of the catalyst, preferable is a method of supporting a powder component on a support in an apparatus having a flat or uneven disk at the bottom of a fixed cylindrical container by vigorously stirring the support charged in the container by repeated rotation movement and orbital movement of the support itself induced by rotating the disk at a high speed and adding the pre-baked powder and, if necessary, the molding aid and the strengthening agent thereto. At the supporting, it is preferable to use a binder. Specific examples of usable binder include water, ethanol, methanol, propanol, polyhydric alcohols, polyvinyl alcohol as a polymeric binder, an aqueous silica sol solution as an inorganic binder and the like but ethanol, methanol, propanol and polyhydric alcohols are preferable. diols such as ethylene glycol and triols such as glycerin are preferable, and an aqueous solution having a glycerin concentration of 5% by weight or more is preferable. By using an aqueous glycerin solution in an appropriate amount, moldability is improved and a high-performance catalyst having a high mechanical strength and a high activity is obtained.

The amount of the binder to he used is usually 2 to 60 parts by weight based on 100 parts by weight of the pre-baked powder but is preferably 10 to 30 parts by weight in the case of the aqueous glycerin solution. At the supporting, the binder may be mixed with the pre-baked powder beforehand or may be added with supplying the pre-baked powder into the tumbling granulator.

As the inactive support, one having a diameter of about 2 to 15 mm is usually used and the pre-baked powder is supported thereon. The amount thereof to be supported is determined in consideration of catalyst use conditions, such as space velocity and concentration of the raw material hydrocarbon, but is usually 20 to 80% by weight.

The molded catalyst is again baked before used in the reaction. The baking temperature at the re-baking is usually 450 to 650° C. and the baking time is usually 3 to 30 hours, preferably 4 to 15 hours, which are appropriately set depending on the reaction conditions to be used. At the time, with regard to the baking temperature of the catalyst to be placed at the raw material gas inlet side, independent of the composition, it is preferable to suppress the activity by baking the catalyst at a temperature higher than that in the case of the catalyst at the gas outlet side. The atmosphere of the baking may be either air atmosphere or nitrogen atmosphere, but industrially, air atmosphere is preferable.

The thus obtained catalyst can be used in the process of producing acrolein and acrylic acid by subjecting propylene to vapor-phase catalytic oxidation with molecular oxygen or a gas containing molecular oxygen or in the process of producing methacrolein and methacrylic acid by subjecting isobutylene, tertiary butanol to vapor-phase catalytic oxidation with molecular oxygen or a gas containing molecular oxygen. In the production process of the invention, the method of flow of the raw material gas may be either a usual single flow method or a recycle method and can be carried out under conditions commonly used without particular limitation. For example, a mixed gas composed of preferably 1 to 10% by volume, more preferably 4 to 9% by volume of propylene, isobutylene, tertiary butanol as a starting raw material substance, preferably 20% by volume, more preferably 4 to 18% by volume of molecular oxygen, preferably 0 to 60% by volume, more preferably 4 to 50% by volume of water vapor, and preferably 20 to 80% by volume, more preferably 30 to 60% by volume of an inert gas such as carbon dioxide or nitrogen gas is introduced onto the catalyst of the invention packed in a reaction tube at 250 to 450° C. under a pressure of normal pressure to 10 atm at a space velocity of 300 to 5000 h$^{-1}$ to perform the reaction. The above reaction can be also carried out using single one kind of the catalyst in the catalyst layer but, in the process of the invention, the hot spot temperature can be lowered by placing catalyst layers divided into N layers (N is an integer of 2 or more).

In the process of the invention, among the catalyst layers formed by division into a plurality of layers in a raw material gas flow direction of the reaction tube, a catalyst layer present closest to a reaction gas inlet side is regarded as Zin and a catalyst layer present closest to a reaction gas outlet side is regarded as Zout, and a catalyst is packed so that activity of the catalyst packed in Zout becomes higher than activity of the catalyst packed in Zin to satisfy the following expression (1):

$$0.5 \leq Cmax - Ccrs \leq 5 \qquad \text{expression (1)}$$

Cmax: a raw material conversion rate at which yield of the objective products becomes maximum;

Ccrs: a raw material conversion rate at which, when maximum temperature of the catalyst layer Zin is regarded as Tin, maximum temperature of the catalyst layer Zout is regarded as Tout, and the raw material conversion rate is changed, a high and low correlation between Tin and Tout is reversed.

More specifically, the composition, baking temperature, mixing ratio with the inert material and packing length of the catalyst at the raw material gas inlet side and the composition, baking temperature and packing length of the catalyst at the raw material gas outlet side are determined so as to satisfy $0.5 \leq Cmax - Ccrs \leq 5$. In this connection, Cmax−Ccrs changes also with the passage of running time but, in order to exhibit the effect of the invention, it is preferable to satisfy $0.5 \leq Cmax - Ccrs \leq 5$ for at least 1 year from the beginning of use of the catalyst, preferably until the catalyst is exchanged. This is because the catalyst immediately after the beginning of the use tends to have particularly a large value of Zout owing to a small raw material conversion rate. Moreover, Cmax−Ccrs generally tends to become small owing to deterioration of the catalyst packed at Zin with the passage of time. Therefore, although it depends on the catalyst used, the effect of the invention can be maintained over a long period of time by designing the packing schedule so that the value is larger than 0.5, preferably 1 or more at the beginning of the reaction. For the above investigation, before the use in an industrial plant, it is preferable to determine the packing condition of the catalyst at an experimental apparatus capable of testing under the same conditions and it is also possible to use simulation on a computer in combination.

For the simulation on a computer, the use of CFD (Computational Fluid Dynamics) is common. By calculation with applying data such as physical properties of the catalyst to be used, the reaction rate constant and heat of reaction to a commercially available software, the raw material conversion rate, yields of acrolein, acrylic acid and the like, and temperature distribution in the catalyst layers under desired reaction conditions can be caluculated.

In an industrial plant or an experimental apparatus, at the determination of Cmax and Ccrs, the temperature distribution of the catalyst layer is measured at a measurement width of 10 cm or less by means of a thermocouple. When measured at a measurement width of more than 10 cm, the temperature of a hot spot cannot be accurately grasped in some cases, so that the case is not preferable. Moreover, with regard to the conversion rate of the raw material gas, the reaction bath temperature is intentionally changed and the raw material conversion rate at each reaction bath temperature, the yield of effective component at each raw material conversion rate, and the hot spot temperature are measured and graphed, and Cmax and Ccrs are determined by interpolation of the data. More accurate data can be obtained by changing the reaction bath temperature at a measurement width of less than 5° C.

According to the invention, by controlling Cmax−Ccrs to larger than or equal to 0.5, abnormally high hot spot temperature of the catalyst at the raw material gas outlet side (i.e., Tout) can be avoided in almost all the reaction tubes even when deviation of the reaction temperature, deviation in the gas flow condition, and deviation in the pressure difference among the reaction tubes inside the reactor are present, and thus it becomes possible to perform steady and safe running. Moreover, by controlling Cmax−Ccrs to smaller than or equal to 5, Tin can be regulated to a relatively low temperature.

As mentioned above, delicate regulation of the catalyst packing schedule is required depending on the running conditions, but it becomes possible to change the packing schedule relatively easily by controlling the baking temperature at preparation of the catalyst to be used at the raw material gas inlet side higher than the baking temperature at preparation of the catalyst to be used at the gas outlet side and diluting the catalyst using an inert material as in the invention. With regard to the effect of the invention, as a matter of course, its easiness of occurrence and degree vary depending on the composition and shape of the catalyst, reaction conditions and the like and hence one cannot make sweeping generalization but, there is a tendency that the above effect becomes more remarkable in the case where the inner diameter of the reaction tube to be used is 25 mm or more or in the case where the molar ratio of water to a starting material gas, propylene is 3.0 or less. Moreover, such an effect is most suitably realized in the case of the aforementioned supported catalyst.

EXAMPLES

The following will further specifically explain the invention with reference to Examples but the invention is not limited to Examples.

The conversion rate, selectivity and yield are defined as follows, respectively.

Propylene conversion rate (% by mol)=(Number of moles of reacted propylene)/(number of moles of supplied propylene)×100

Acrolein yield (% by mol)=(Number of moles of produced acrolein)/(number of moles of supplied propylene)×100

Acrylic acid yield (% by mol)=(Number of moles of produced acrylic acid)/(number of moles of supplied propylene)×100

In the case of using isobutylene and/or tertiary butanol instead of propylene as a raw material, acrolein can be replaced with methacrolein and acrylic acid can be replaced with metacrylic acid.

Example 1

(Preparation of Catalyst)

An aqueous solution (A1) was obtained by dissolving 423.8 parts by weight of ammonium molybdate and 1.64 parts by weight of potassium nitrate with heating and stirring 3000 parts by weight of distilled water. Separately, an aqueous solution (B1) was prepared by dissolving 302.7 parts by weight of cobalt nitrate, 162.9 parts by weight of nickel nitrate and 145.4 parts by weight of ferric nitrate in 1000 parts by weight of distilled water and an aqueous solution (C1) was prepared by dissolving 164.9 parts by weight of bismuth nitrate in 200 parts by weight of distilled water acidified by adding 42 parts by weight of conc. nitric acid. (B1) and (C1) were sequentially mixed into the above aqueous solution (A1) with vigorous stirring and the formed suspension was dried by means of a spray drier and baked at 440° C. for 6 hours to obtain a pre-baked powder (D1). The compositional ratio of the catalyst active component excluding oxygen at this time was Mo=12, Bi=1.7, Ni=2.8, Fe=1.8, Co=5.2 and K=0.15 as an atomic ratio.

Thereafter, a powder obtained by mixing 5 parts by weight of crystalline cellulose with 100 parts by weight of the pre-baked powder was supported on an inert support (a spherical material having a diameter of 4.5 mm, composed of alumina, silica, as main components) and molded into a sphere having a diameter of 5.2 mm so as to result in a ratio of 50% by weight based on the catalyst after molding using a 20% by weight aqueous glycerin solution as a binder, thereby obtaining a supported catalyst (E1).

The supported catalyst (E1) was baked at a baking temperature of 530° C. for 4 hours under an air atmosphere and thereby a catalyst (F1) was obtained.

Then, 423.8 parts by weight of ammonium molybdate and 1.08 parts by weight of potassium nitrate were dissolved with heating and stirring 3000 parts by weight of distilled water to obtain an aqueous solution (A2). Separately, an aqueous solution (B2) was prepared by dissolving 302.7 parts by weight of cobalt nitrate, 162.9 parts by weight of nickel nitrate and 145.4 parts by weight of ferric nitrate in 1000 parts by weight of distilled water and an aqueous solution (C2) was prepared by dissolving 164.9 parts by weight of bismuth nitrate in 200 parts by weight of distilled water acidified by adding 42 parts by weight of conc. nitric acid. (B2) and (C2) were sequentially mixed into the above aqueous solution (A2) with vigorous stirring and the formed suspension was dried by means of a spray drier and baked at 440° C. for 6 hours to obtain a pre-baked powder (D2). The compositional ratio of the catalyst active component excluding oxygen at this time is Mo=12, Bi=1.7, Ni=2.8, Fe=1.8, Co=5.2 and K=0.10 as an atomic ratio.

Thereafter, a powder obtained by mixing 5 parts by weight of crystalline cellulose with 100 parts by weight of the pre-baked powder was supported on an inert support (a spherical material having a diameter of 4.5 mm, composed of alumina, silica as main components) and molded into a sphere having a diameter of 5.2 mm so as to result in a ratio of 50% by weight based on the catalyst after molding using a 20% by weight aqueous glycerin solution as a binder, thereby obtaining a supported catalyst (E2).

The supported catalyst (F2) was baked at a baking temperature of 530° C. for 4 hours and thereby a catalyst (F2) was obtained. The supported catalyst (E2) was baked at a baking temperature of 510° C. for 4 hours and thereby a catalyst (F3) was obtained.

(Oxidation Reaction Test)

From a raw material gas inlet side of a stainless reactor having an inner diameter of 25.4 mm, fitted on its tube axis with a jacket for circulating a molten salt as a heating medium and a thermocouple for measuring catalyst layer temperature, a silica-alumina sphere having a diameter of 5.2 mm in a length of 20 cm, a diluted catalyst obtained by mixing the oxidation catalyst (F1) with a silica-alumina mixture inactive support having a diameter of 5.2 mm in a weight ratio of 4:1 as a first layer of oxidation catalyst layer (raw material gas inlet side) in a length of 100 cm, and the oxidation catalyst (F3) as a second layer of oxidation catalyst (gas outlet side) in a length of 250 cm were packed therein in this order, and the reaction bath temperature was set at 330° C. A gas in which the supplying amounts of propylene, air, nitrogen and water had been set so that the raw material molar ratio became as follows: propylene:oxygen:nitrogen:water=1:1.7:8.8:1 was introduced into the oxidation reactor at a space velocity of 1500 h$^{-1}$ and the outlet pressure of the reactor was set at 70 kPaG. When 200 hours had passed after the start of the reaction, the reaction bath temperature was changed at an interval of 2° C. to carry out a test of measuring the raw material conversion rate, acrolein and acrylic acid yields, and hot spot temperature (hereinafter referred to as reaction temperature-changing test). Upon the test, the raw material conversion rate was 97.8% and the total yield of acrolein and acrylic acid was 91.8% at maximum. The reaction bath temperature at this time was 330° C., the hot spot temperature of the catalyst layer at the gas inlet side was 434° C. and the hot spot temperature of the catalyst layer at the gas outlet side was 378° C. Moreover, a high and low relation between these two hot spot temperatures was reversed at the raw material conversion rate of 95.5%. Namely, Cmax–Ccrs was 2.3. At the reaction bath temperature of 320° C., the propylene conversion rate became 93% but the hot spot temperature of the catalyst layer at the gas inlet side was 352° C. and the hot spot temperature of the catalyst layer at the gas outlet side was 401° C. Thus, even in the case where the propylene conversion rate decreased in a large degree, the hot spot temperature of the catalyst layer at the gas outlet side did not become extremely high and it was suggested that stable operation be possible over a long period of time.

Example 2

An oxidation reaction of propylene was carried out in the same manner as in Example 1 except that the catalyst packed in the raw material gas inlet area was changed to a diluted catalyst obtained by mixing F2 with a silica-alumina mixture inactive support having a diameter of 5.2 mm in a weight ratio of 4:1 in a length of 120 cm and the catalyst packed in the raw material gas outlet area was changed to the F3 catalyst in a length of 230 cm in the oxidation reaction conditions of Example 1.

When the reaction temperature-changing test was carried out, the raw material conversion rate was 97.2% and the total yield of acrolein and acrylic acid was 92.1% at maximum. The reaction bath temperature at this time was 332° C., the hot spot temperature of the catalyst layer at the gas inlet side was 431° C. and the hot spot temperature of the catalyst layer at the gas outlet side was 372° C. Moreover, a high and low relation between these two hot spot temperatures was reversed at the raw material conversion rate of 95.1%. Namely, Cmax–Ccrs was 2.1. At the reaction bath temperature of 322° C., the propylene conversion rate became 93% but the hot spot temperature of the catalyst layer at the gas inlet side was 353° C. and the hot spot temperature of the catalyst layer at the gas outlet side was 398° C. Thus, even in the case where the propylene conversion rate decreased in a large degree, the hot spot temperature of the catalyst layer at the gas outlet side did not become extremely high and it was suggested that stable operation be possible over a long period of time.

Example 3

When a test was carried out in the same manner as in Example 2 except that a gas in which the supplying amounts of propylene, air, nitrogen and water had been set so that the raw material, molar ratio became as follows: propylene:oxygen:nitrogen:water=1:1.8:10:1.5 was introduced into the oxidation reactor at a space velocity of 1500 h$^{-1}$ and the outlet pressure of the reactor was set at 55 kPaG in Example 2, the raw material conversion rate was 97.9% and the total yield of acrolein and acrylic acid was 92.3% at maximum. The reaction bath temperature at this time was 330° C., the hot spot temperature of the catalyst layer at the gas inlet side was 424° C. and the hot spot temperature of the catalyst layer at the gas outlet side was 370° C. Moreover, a high and low relation between these two hot spot temperatures was reversed at the raw material conversion rate of 96.2%. Namely, Cmax–Ccrs was 1.7. At the reaction bath temperature of 318° C., the propylene conversion, rate became 95% but the hot spot temperature of the catalyst layer at the gas inlet side was 348° C. and the hot spot temperature of the catalyst layer at the gas outlet side was 410° C. Thus, even in the case where the propylene conversion rate decreased in a large degree, the hot spot temperature of the catalyst layer at the gas outlet side did not become extremely high and it was suggested that stable operation be possible over a long period of time.

Example 4

When a test was carried out in the same manner as in Example 3 except that the gas was introduced into the oxidation reactor at a space velocity of 1715 h$^{-1}$ and the outlet pressure of the reactor was set at 70 kPaG in Example 3, the raw material conversion rate was 97.8% and the total yield of acrolein and acrylic acid was 91.6% at maximum. The reaction bath temperature at this time was 332° C., the hot spot temperature of the catalyst layer at the gas inlet side was 429° C. and the hot spot temperature of the catalyst layer at the gas outlet side was 371° C. Moreover, a high and low relation between these two hot spot temperatures was reversed at the raw material conversion rate of 96.1%. Namely, Cmax–Ccrs was 1.7. At the reaction bath temperature of 319° C., the propylene conversion rate became 95% but the hot spot temperature of the catalyst layer at the gas inlet side was 350° C. and the hot spot temperature of the catalyst layer at the gas outlet side was 414° C. Thus, even in the case where the propylene conversion rate decreased in a large degree, the hot spot temperature of the catalyst layer at the gas outlet side did not become extremely high and it was suggested that stable operation be possible over a long period of time.

Example 5

When a test was carried out in the same manner as in Example 2 except that a gas in which the supplying amounts of propylene, air, nitrogen and water had been set so that the raw material molar ratio became as follows: propylene:oxygen:nitrogen:water=1:1.9:12:1 was introduced into the oxidation reactor at a space velocity of 2000 h$^{-1}$, the outlet pressure of the reactor was set at 65 kPaG and acrolein was designated as the objective product in Example 2, the raw material conversion rate was 96.5% and the yield of acrolein was 85.2% at maximum. The reaction bath temperature at this time was 334° C., the hot spot temperature the catalyst layer at the gas inlet side was 420° C. and the hot spot temperature the catalyst layer at the gas outlet side was 385° C. Moreover, a high and low relation between these two hot spot temperatures was reversed at the raw material conversion rate of 95.5%. Namely, Cmax-Ccrs was 1.0. At the reaction bath temperature of 326° C., the propylene conversion rate became 94% but the hot spot temperature of the catalyst layer at the gas inlet side was 347° C. and the hot spot temperature of the catalyst layer at the gas outlet side was 415° C. Thus, even in the case where the propylene conversion rate decreased in a large degree, the hot spot temperature of the catalyst layer at the gas outlet side did not become extremely high and it was suggested that stable operation be possible over a long period of time.

Example 6

From a raw material gas inlet side of a stainless reactor having an inner diameter of 27.2 mm, fitted on its tube axis with a jacket for circulating a molten salt as a heating medium and a thermocouple for measuring catalyst layer temperature, a silica-alumina sphere having a diameter of 5.2 mm in a length of 20 cm, a diluted catalyst obtained by mixing the oxidation catalyst (F1) with a silica-alumina mixture inactive support having a diameter of 5.2 mm in a weight ratio of 3:1 as a first layer of oxidation catalyst layer (raw material gas inlet side) in a length of 100 cm and the oxidation catalyst (F3) as a second layer of oxidation catalyst (gas outlet side) in a length of 210 cm were packed therein in this order, and the reaction bath temperature was set at 325° C. A gas in which the supplying amounts of propylene, air, nitrogen and water had been set so that the raw material molar ratio became as follows: propylene:oxygen:nitrogen:water=1:1.7:8.8:1 was introduced into the oxidation reactor at a space velocity of 1250 h$^{-1}$ and the outlet pressure of the reactor was set at 50 kPaG. When 200 hours had passed after the start of the reaction, the reaction bath temperature was changed at an interval of 2° C. to carry out the reaction temperature-changing test. Upon the test, the raw material conversion rate was 97.8% and the total yield of acrolein and acrylic acid was 91.5% at maximum. The reaction bath temperature at this time was 322° C., the hot spot temperature of the catalyst layer at the gas inlet side was 424° C. and the hot spot temperature of the catalyst layer at the gas outlet side was 373° C. Moreover, a high and low relation between these two hot spot temperatures was reversed at the raw material conversion rate of 96.6%. Namely, Cmax-Ccrs was 1.2. A1 the reaction bath temperature of 310° C. the propylene conversion rate became 92% but the hot spot temperature of the catalyst layer at the gas inlet side was 330° C. and the hot spot temperature of the catalyst layer at the gas outlet side was 400° C. Thus, even in the case where the propylene conversion rate decreased in a large degree, the hot spot temperature of the catalyst layer at the gas outlet side did not become extremely high and it was suggested that stable operation be possible over a long period of time.

Comparative Example 1

An oxidation reaction of propylene was carried out in the same manner as in Example 1 except that the catalyst packed in the raw material gas inlet area was changed to a diluted catalyst obtained by mixing F3 with a silica-alumina mixture inactive support having a diameter of 5.2 mm in a weight ratio of 2:1 in a length of 100 cm and the catalyst packed in the raw material gas outlet area was changed to the F3 catalyst in a length of 250 cm in the oxidation reaction conditions of Example 1.

When the reaction temperature-changing test was carried out, the raw material conversion rate was 98.5% and the total yield of acrolein and acrylic acid was 91.9% at maximum. The reaction bath temperature at this time was 335° C., the hot spot temperature of the catalyst layer at the gas inlet side was 418° C. and the hot spot temperature of the catalyst layer at the gas outlet side was 380° C. Moreover, a high and low relation between these two hot spot temperatures was reversed at the raw material conversion rate of 98.2%. Namely, Cmax-Ccrs was 0.3. At the reaction bath temperature of 326° C., the propylene conversion rate became 95.5% but the hot spot temperature of the catalyst layer at the gas inlet side was 358° C. and the hot spot temperature of the catalyst layer at the gas outlet side was 4415° C. As compared with Examples, in the case where the propylene conversion rate decreased in a large degree, the hot spot temperature of the catalyst layer at the gas outlet side became extremely high.

Industrial Applicability

According to the invention, it becomes possible to produce acrolein and acrylic acid or methacrolein and methacrylic acid safely and steadily in high yields.

While the invention has been described in detail and with reference to specific embodiments thereof, it will be apparent to one skilled in the art that various changes and modifications can be made therein without departing from the spirit and scope thereof.

The present application is based on Japanese Patent Application No. 2011-20782 and Japanese Patent Application No. 2011-20783 both filed on Feb. 2, 2011, and the contents are incorporated herein by reference. Also, all the references cited herein are incorporated as a whole.

The invention claimed is:

1. A process for producing acrolein and acrylic acid or methacrolein and methacrylic acid by subjecting propylene or at least one kind selected from isobutylene and tertiary butanol to vapor-phase catalytic oxidation with a gas containing molecular oxygen using a fixed bed multitubular reactor, the process comprising:

A) providing a plurality of catalyst layers formed by division into N, where N represents an integer of 2 or more, in a raw material gas flow direction of reaction tubes and regarding the catalyst layer present closest to a reaction gas inlet side among the catalyst layers as Zin and the catalyst layer present closest to a reaction gas outlet side among the catalyst layers as Zout; and B) packing a catalyst so that activity of the catalyst packed in Zout becomes higher than activity of the catalyst packed in Zin to satisfy the following expression (1):

$$0.5 \leq Cmax-Ccrs \leq 5 \qquad \text{expression (1)}$$

Cmax: the raw material conversion rate at which yield of the objective products becomes maximum; and Ccrs: the raw material conversion rate at which, when maximum temperature of the catalyst layer Zin is regarded as Tin, maximum temperature of the catalyst layer Zout is regarded as Tout, and the raw material conversion rate changes from Cmax to a raw material conversion rate other than Cmax, Tout>Tin; a wherein said catalyst has the formula:

where Mo, Bi, Ni, Co and Fe represent molybdenum, bismuth, nickel, cobalt and iron, respectively; X represents at least one element selected from tungsten, antimony, tin, zinc, chromium, manganese, magnesium, silica, aluminum, cerium and titanium; Y represents at least one element selected from potassium, rubidium, thallium and cesium; and a, b, c, d, f, g, h and x represent the numbers of atoms of molybdenum, bismuth, nickel, cobalt, iron, X, Y and oxygen, respectively, such that $a=12$, $b=0.1$ to 7, $c+d=0.5$ to 20, $f=0.5$ to 8, $g=0$ to 2, $h=0.005$ to 2, and x is a value determined by the oxidation state of the individual elements.

2. The process for producing acrolein and acrylic acid or methacrolein and methacrylic acid according to claim 1,
wherein N is 3 or less, baking temperature of the catalyst packed in Zin is higher than baking temperature of the catalyst packed in Zout, and
a mixture of the catalyst and a molded body of an inactive material is packed in Zin.

3. The process for producing acrolein and acrylic acid or methacrolein and methacrylic acid according to claim 1,
wherein the catalyst is a spherical supported catalyst obtained by supporting an active powder on an inactive material.

4. The process for producing acrolein and acrylic acid or methacrolein and methacrylic acid according to claim 1,
wherein particle diameter of the catalyst packed in each catalyst layer is the same over all the layers.

5. the process for producing acrolein and acrylic acid or methacrolein and methacrylic acid according to claim 1,
wherein in said formula, $b=0.5$ to 4, $c+d=1$ to 12, $f=0.5$ to 5, $g=0$ to 1, and $h=0.01$ to 0.5.

* * * * *